US010888535B2

(12) United States Patent
Shiozaki et al.

(10) Patent No.: US 10,888,535 B2
(45) Date of Patent: Jan. 12, 2021

(54) SKIN DISINFECTANT COMPOSITION

(71) Applicant: OTSUKA PHARMACEUTICAL FACTORY, INC., Tokushima (JP)

(72) Inventors: Mari Shiozaki, Tokushima (JP); Ryohei Tsubakiyama, Tokushima (JP); Motoya Kikuchi, Tokushima (JP); Kaoru Imai, Tokushima (JP); Akifumi Hagi, Tokushima (JP)

(73) Assignee: OTSUKA PHARMACEUTICAL FACTORY, INC., Tokushima (JP)

(*) Notice: Subject to any disclaimer, the term of this patent is extended or adjusted under 35 U.S.C. 154(b) by 0 days.

(21) Appl. No.: 15/781,424

(22) PCT Filed: Nov. 30, 2016

(86) PCT No.: PCT/JP2016/005015
§ 371 (c)(1),
(2) Date: Jun. 4, 2018

(87) PCT Pub. No.: WO2017/098702
PCT Pub. Date: Jun. 15, 2017

(65) Prior Publication Data
US 2019/0000783 A1    Jan. 3, 2019

(30) Foreign Application Priority Data

Dec. 7, 2015 (JP) ................. 2015-238403

(51) Int. Cl.
| *A61K 31/155* | (2006.01) |
| *A61K 47/18* | (2017.01) |
| *A61K 47/20* | (2006.01) |
| *A61K 47/32* | (2006.01) |
| *A61P 31/04* | (2006.01) |
| *A61K 47/12* | (2006.01) |

(52) U.S. Cl.
CPC ............ *A61K 31/155* (2013.01); *A61K 47/12* (2013.01); *A61K 47/18* (2013.01); *A61K 47/20* (2013.01); *A61K 47/32* (2013.01); *A61P 31/04* (2018.01)

(58) Field of Classification Search
CPC ................. A61P 31/04; A61P 31/02
See application file for complete search history.

(56) References Cited

U.S. PATENT DOCUMENTS

| 5,154,850 | A | 10/1992 | Deguchi et al. | |
| 5,266,598 | A | 11/1993 | Ninomiya et al. | |
| 7,825,080 | B2 * | 11/2010 | Miyata ................ | A01N 47/44 422/28 |
| 2005/0214240 | A1 * | 9/2005 | Ito ......................... | A61K 8/553 424/70.23 |
| 2006/0189500 | A1 | 8/2006 | Miyata et al. | |
| 2007/0025948 | A1 * | 2/2007 | Saito .................... | A01N 47/44 424/70.31 |
| 2007/0041866 | A1 | 2/2007 | Miyata et al. | |
| 2007/0253909 | A1 | 11/2007 | Magallon et al. | |
| 2007/0254854 | A1 | 11/2007 | Magallon et al. | |
| 2008/0108674 | A1 | 5/2008 | Magallon et al. | |
| 2010/0331423 | A1 | 12/2010 | Miyata et al. | |
| 2014/0235727 | A1 * | 8/2014 | Tufts ..................... | A61L 15/44 514/635 |

FOREIGN PATENT DOCUMENTS

| EP | 1570839 A1 | 9/2005 |
| EP | 1634499 A1 | 3/2006 |
| EP | 2499913 A1 | 9/2012 |
| JP | 2005-289959 A | 10/2005 |
| WO | 2009/058144 A1 | 5/2009 |

OTHER PUBLICATIONS

Nagai et al., "Antiseptic Effect of OPB-2045 Solution Applied to Normal Skin", KankyoKansen, 15(3), pp. 220, 2000 (with partial translation).
"5% Chlorhexidine Gluconate Solution OY", no Tenpu Bunsho, 7th edition, Nichi-iko Pharmaceutical Co., Ltd., Column of composition, Sep. 2009 (No translation but ISR & IPRP are the concise explanation of the relevance).
"Maskin Solution (5wv%)", no Tenpu Bunsho, 5th edition, Maruishi Parmaceutical Co., Ltd., Column of composition, Jun. 2008 (No translation but ISR & IPRP are the concise explanation of the relevance).
International Search Report issued with respect to Application No. PCT/JP2016/005015, dated Dec. 27, 2016.
International Preliminary Report on Patentability issued with respect to Application No. PCT/JP2016/005015, dated Jun. 12, 2018.

* cited by examiner

*Primary Examiner* — Sahar Javanmard
(74) *Attorney, Agent, or Firm* — Greenblum & Bernstein, P.L.C.

(57) ABSTRACT

It is to provide a disinfectant liquid which enables easy identification of the application sites in preoperative skin disinfection and the like, where the liquid is obtained by coloring an aqueous solution of olanexidine gluconate which is a colorless and transparent liquid. A disinfectant liquid comprises olanexidine gluconate, a coloring agent such as Sunset Yellow FCF, an alkyl dimethylamine oxide such as lauryl dimethylamine oxide, and optionally one or more surfactants other than alkyl dimethylamine oxide such as polyoxyethylene alkyl ether including lauromacrogol and polyoxyethylene polyoxypropylene alkyl ether including polyoxyethylene(20) polyoxypropylene(4) cetyl ether. The disinfectant liquid enables easy identification of the application sites in preoperative skin disinfection and the like.

19 Claims, 11 Drawing Sheets

[Figure 1]

| | Test bacteria | Bactericidal efficacy | |
|---|---|---|---|
| | | 30 seconds | 60 seconds |
| Colored Olanedine disinfectant liquid formulation* | Staphylococcus aureus ATCC29213 | ○ | ○ |
| | Enterococcus faecalis ATCC15606 | ○ | ○ |
| | Staphylococcus epidermidis ATCC12228 | ○ | ○ |
| | Serratia marcescens ATCC14756 | ○ | ○ |
| | Acinetobacter baumannii ATCC19606 | ○ | ○ |
| | Escherichia coli ATCC25922 | ○ | ○ |
| | Pseudomonas aeruginosa ATCC27853 | ○ | ○ |
| | Candida albicans ATCC90028 | × | ○ |

*2% lauromacrogol was added

[Figure 2]

| | Test bacteria | Initial cell count | Log reduction | |
|---|---|---|---|---|
| | | | 30 seconds | 60 seconds |
| Colorless Olanedine disinfectant liquid formulation | Staphylococcus aureus ATCC29213 | $10^{6.1}$ | >5.1 | >5.1 |
| Colored Olanedine disinfectant liquid formulation* | | | >5.1 | >5.1 |
| Colorless Olanedine disinfectant liquid formulation | Enterococcus faecalis ATCC15606 | $10^{6.5}$ | >5.5 | >5.5 |
| Colored Olanedine disinfectant liquid formulation* | | | >5.5 | >5.5 |
| Colorless Olanedine disinfectant liquid formulation | Staphylococcus epidermidis ATCC12228 | $10^{6.1}$ | >5.1 | >5.1 |
| Colored Olanedine disinfectant liquid formulation* | | | >5.1 | >5.1 |
| Colorless Olanedine disinfectant liquid formulation | Serratia marcescens ATCC14756 | $10^{5.6}$ | >4.6 | >4.6 |
| Colored Olanedine disinfectant liquid formulation* | | | >4.6 | >4.6 |
| Colorless Olanedine disinfectant liquid formulation | Acinetobacter baumannii ATCC19606 | $10^{5.3}$ | >4.3 | >4.3 |
| Colored Olanedine disinfectant liquid formulation* | | | >4.3 | >4.3 |
| Colorless Olanedine disinfectant liquid formulation | Escherichia coli ATCC25922 | $10^{5.5}$ | >4.5 | >4.5 |
| Colored Olanedine disinfectant liquid formulation* | | | >4.5 | >4.5 |
| Colorless Olanedine disinfectant liquid formulation | Pseudomonas aeruginosa ATCC27853 | $10^{4.2}$ | >3.2 | >3.2 |
| Colored Olanedine disinfectant liquid formulation* | | | >3.2 | >3.2 |
| Colorless Olanedine disinfectant liquid formulation | Candida albicans ATCC90028 | $10^{4.7}$ | >3.7 | >3.7 |
| Colored Olanedine disinfectant liquid formulation* | | | 3.3 | >3.7 |

*2% lauromacrogol was added

[Figure 3]

| | Surfactant [addition amount] | Bactericidal efficacy | |
|---|---|---|---|
| | | 30 seconds | 60 seconds |
| Colored Olanedine disinfectant liquid formulation 1 | Lauromacrogol [2%] | × | ○ |
| Colored Olanedine disinfectant liquid formulation 2 | Polyoxyethylene(20) polyoxypropylene(8) glycol [3.6%] | × | × |
| Colored Olanedine disinfectant liquid formulation 3 | Polyoxyethylene hardened castor oil 60 [6%] | × | × |
| Colored Olanedine disinfectant liquid formulation 4 | Lauryl dimethylamine oxide [2.4%] | ○ | ○ |

[Figure 4]

|  | Surfactant [addition amount] | Initial cell count | Log reduction | |
|---|---|---|---|---|
|  |  |  | 30 seconds | 60 seconds |
| Colorless Olanedine disinfectant liquid formulation | - | $10^{4.7}$ | >3.7 | >3.7 |
| Colored Olanedine disinfectant liquid formulation 1 | Lauromacrogol [2%] |  | 3.3 | >3.7 |
| Colored Olanedine disinfectant liquid formulation 2 | Polyoxyethylene(20) polyoxypropylene(8) glycol [3.6%] |  | 1.7 | 2.7 |
| Colored Olanedine disinfectant liquid formulation 3 | Polyoxyethylene hardened castor oil 60 [6%] |  | 1.4 | 2.2 |

|  | Surfactant [addition amount] | Initial cell count | Log reduction | |
|---|---|---|---|---|
|  |  |  | 30 seconds | 60 seconds |
| Colorless Olanedine disinfectant liquid formulation | - | $10^{5.0}$ | >4.0 | >4.0 |
| Colored Olanedine disinfectant liquid formulation 4 | Lauryl dimethylamine oxide [2.4%] |  | >4.0 | >4.0 |

[Figure 5]

|  | Surfactant [addition amount] | Bactericidal efficacy ||
|---|---|---|---|
|  |  | 30 seconds | 60 seconds |
| Colored Olanedine disinfectant liquid formulation A | Lauryl dimethylamine oxide [2.5%] | ○ | ○ |
| Colored Olanedine disinfectant liquid formulation B | Decyl dimethylamine oxide [2.5%] | ○ | ○ |
| Colored Olanedine disinfectant liquid formulation C | Myristyl dimethylamine oxide [2.5%] | ○ | ○ |
| Colored Olanedine disinfectant liquid formulation D | Cocoalkyl dimethylamine oxide [2.5%] | ○ | ○ |

[Figure 6]

| | Surfactant [addition amount] | Initial cell count | Log reduction | |
|---|---|---|---|---|
| | | | 30 seconds | 60 seconds |
| Colorless Olanedine disinfectant liquid formulation | - | $10^{4.7}$ | >3.7 | >3.7 |
| Colored Olanedine disinfectant liquid formulation A | Lauryl dimethylamine oxide [2.5%] | | >3.7 | >3.7 |
| Colored Olanedine disinfectant liquid formulation B | Decyl dimethylamine oxide [2.5%] | | >3.7 | >3.7 |
| Colored Olanedine disinfectant liquid formulation C | Myristyl dimethylamine oxide [2.5%] | | >3.7 | >3.7 |
| Colored Olanedine disinfectant liquid formulation D | Cocoalkyl dimethylamine oxide [2.5%] | | >3.7 | >3.7 |

[Figure 7]

| Test Number | LDAO | Lauromacrogol | LDAO ratio | 30 sec | 60 sec |
|---|---|---|---|---|---|
| 1 | 2.00 | 0.0 | 1.00 | ○ | ○ |
| 2 | 2.40 | 0.0 | 1.00 | ○ | ○ |
| 3 | 2.91 | 0.0 | 1.00 | ○ | ○ |
| 4 | 1.07 | 1.0 | 0.52 | ○ | ○ |
| 5 | 1.44 | 1.5 | 0.49 | ○ | ○ |
| 6 | 1.07 | 1.6 | 0.40 | ○ | ○ |
| 7 | 0.64 | 1.5 | 0.30 | ○ | ○ |
| 8 | 0.80 | 2.0 | 0.29 | ○ | ○ |
| 9 | 0.64 | 2.0 | 0.24 | ○ | ○ |
| 10 | 0.48 | 2.0 | 0.19 | ○ | ○ |
| 11 | 0.45 | 2.0 | 0.18 | ○ | ○ |
| 12 | 0.40 | 2.0 | 0.17 | × | ○ |
| 13 | 0.32 | 2.0 | 0.14 | × | ○ |
| 14 | 0.64 | 4.0 | 0.14 | × | ○ |
| 15 | 0.21 | 1.6 | 0.12 | × | ○ |
| 16 | 0.21 | 2.0 | 0.10 | × | ○ |
| 17 | 0.21 | 4.0 | 0.05 | × | × |
| 18 | 0.00 | 2.0 | 0.00 | × | ○ |

[Figure 8]

| Test Number | LDAO | Lauromacrogol | LDAO ratio | Initial cell count | Log reduction | |
|---|---|---|---|---|---|---|
| | | | | | 30 seconds | 60 seconds |
| Colorless Olanedine disinfectant liquid formulation | - | - | - | $10^{4.9}$ | >3.9 | >3.9 |
| 1 | 2.00 | 0.0 | 1.00 | | >3.9 | >3.9 |
| 18 | 0.00 | 2.0 | 0.00 | | 2.3 | >3.9 |

| Test Number | LDAO | Lauromacrogol | LDAO ratio | Initial cell count | Log reduction | |
|---|---|---|---|---|---|---|
| | | | | | 30 seconds | 60 seconds |
| Colorless Olanedine disinfectant liquid formulation | - | - | - | $10^{5.2}$ | >4.2 | >4.2 |
| 3 | 2.91 | 0.0 | 1.00 | | >4.2 | >4.2 |
| 4 | 1.07 | 1.0 | 0.52 | | >4.2 | >4.2 |
| 6 | 1.07 | 1.6 | 0.40 | | >4.2 | >4.2 |
| 7 | 0.64 | 1.5 | 0.30 | | >4.2 | >4.2 |
| 15 | 0.21 | 1.6 | 0.12 | | 3.9 | >4.2 |
| 16 | 0.21 | 2.0 | 0.10 | | 3.4 | >4.2 |
| 17 | 0.21 | 4.0 | 0.05 | | 1.8 | 3.6 |

| Test Number | LDAO | Lauromacrogol | LDAO ratio | Initial cell count | Log reduction | |
|---|---|---|---|---|---|---|
| | | | | | 30 seconds | 60 seconds |
| Colorless Olanedine disinfectant liquid formulation | - | - | - | $10^{5.0}$ | >4.0 | >4.0 |
| 2 | 2.40 | 0.0 | 1.00 | | >4.0 | >4.0 |
| 5 | 1.44 | 1.5 | 0.49 | | >4.0 | >4.0 |
| 11 | 0.45 | 2.0 | 0.18 | | >4.0 | >4.0 |
| 12 | 0.40 | 2.0 | 0.17 | | 3.8 | >4.0 |

| Test Number | LDAO | Lauromacrogol | LDAO ratio | Initial cell count | Log reduction | |
|---|---|---|---|---|---|---|
| | | | | | 30 seconds | 60 seconds |
| Colorless Olanedine disinfectant liquid formulation | - | - | - | $10^{5.0}$ | >4.0 | >4.0 |
| 8 | 0.80 | 2.0 | 0.29 | | >4.0 | >4.0 |

| Test Number | LDAO | Lauromacrogol | LDAO ratio | Initial cell count | Log reduction | |
|---|---|---|---|---|---|---|
| | | | | | 30 seconds | 60 seconds |
| Colorless Olanedine disinfectant liquid formulation | - | - | - | $10^{5.0}$ | >4.0 | >4.0 |
| 9 | 0.64 | 2.0 | 0.24 | | >4.0 | >4.0 |
| 10 | 0.48 | 2.0 | 0.19 | | >4.0 | >4.0 |
| 13 | 0.32 | 2.0 | 0.14 | | 3.5 | >4.0 |
| 14 | 0.64 | 4.0 | 0.14 | | 2.0 | >4.0 |

[Figure 9]

| Test Number | LDAO | POE(20) POP(4) cetyl ether | LDAO ratio | 30 sec | 60 sec |
|---|---|---|---|---|---|
| 1 | 0.80 | 3.6 | 0.18 | ○ | ○ |
| 2 | 0.48 | 3.6 | 0.12 | ○ | ○ |
| 3 | 0.00 | 3.6 | 0.00 | × | × |

[Figure 10]

| Test Number | LDAO | POE(20) POP(4) cetyl ether | LDAO ratio | Initial cell count | Log reduction 30 seconds | Log reduction 60 seconds |
|---|---|---|---|---|---|---|
| Colorless Olanedine disinfectant liquid formulation | - | - | - | $10^{4.2}$ | >3.2 | >3.2 |
| 1 | 0.80 | 3.6 | 0.18 | | >3.2 | >3.2 |
| 2 | 0.48 | 3.6 | 0.12 | | >3.2 | >3.2 |

| | LDAO | POE(20) POP(4) cetyl ether | LDAO ratio | Initial cell count | Log reduction 30 seconds | Log reduction 60 seconds |
|---|---|---|---|---|---|---|
| Colorless Olanedine disinfectant liquid formulation | - | - | - | $10^{4.7}$ | >3.7 | >3.7 |
| 3 | 0.00 | 3.6 | 0.00 | | 1.7 | 2.7 |

[Figure 11]

| Test Number | LDAO | Lauromacrogol | POE(20) POP(4) cetyl ether | LDAO ratio | 30 sec | 60 sec |
|---|---|---|---|---|---|---|
| 1 | 1.60 | 1.0 | 1.0 | 0.44 | ○ | ○ |
| 2 | 1.44 | 1.5 | 2.0 | 0.29 | ○ | ○ |
| 3 | 0.96 | 1.5 | 1.0 | 0.28 | ○ | ○ |
| 4 | 0.80 | 2.0 | 1.0 | 0.21 | × | ○ |
| 5 | 0.64 | 1.0 | 2.5 | 0.15 | × | ○ |
| 6 | 0.32 | 1.0 | 2.5 | 0.08 | ○ | ○ |
| 7 | 0.21 | 2.0 | 1.0 | 0.07 | × | ○ |
| 8 | 0.21 | 2.0 | 1.5 | 0.06 | × | ○ |

[Figure 12]

| Test Number | LDAO | Lauromacrogol | POE(20) POP(4) cetyl ether | LDAO ratio | Initial cell count | Log reduction | |
|---|---|---|---|---|---|---|---|
| | | | | | | 30 seconds | 60 seconds |
| Colorless Olanedine disinfectant liquid formulation | - | - | | - | $10^{5.4}$ | >4.4 | >4.4 |
| 1 | 1.60 | 1.0 | 1.0 | 0.44 | | >4.4 | >4.4 |
| 3 | 0.96 | 1.5 | 1.0 | 0.28 | | >4.4 | >4.4 |

| Test Number | LDAO | Lauromacrogol | POE(20) POP(4) cetyl ether | LDAO ratio | Initial cell count | Log reduction | |
|---|---|---|---|---|---|---|---|
| | | | | | | 30 seconds | 60 seconds |
| Colorless Olanedine disinfectant liquid formulation | - | - | | - | $10^{4.2}$ | >3.2 | >3.2 |
| 2 | 1.44 | 1.5 | 2.0 | 0.29 | | >3.2 | >3.2 |
| 4 | 0.80 | 2.0 | 1.0 | 0.21 | | 2.7 | >3.2 |
| 5 | 0.64 | 1.0 | 2.5 | 0.15 | | 2.4 | >3.2 |
| 6 | 0.32 | 1.0 | 2.5 | 0.08 | | >3.2 | >3.2 |
| 7 | 0.21 | 2.0 | 1.0 | 0.07 | | 2.1 | >3.2 |
| 8 | 0.21 | 2.0 | 1.5 | 0.06 | | 2.9 | >3.2 |

SKIN DISINFECTANT COMPOSITION

TECHNICAL FIELD

The present invention relates to a disinfectant liquid comprising olanexidine gluconate and enabling easy identification of the application sites in preoperative skin disinfection and the like.

BACKGROUND ART

Olanexidine, whose chemical name is 1-(3,4-dichlorobenzyl)-5-octylbiguanide, is a compound having high bactericidal activity. Studies have been conducted on the bactericidal agents comprising hydrochloride of Olanexidine as active ingredient (see for example, non-patent document 1). Olanexidine and hydrochloride thereof are extremely insoluble in water. The aqueous solution prepared by dissolving olanexidine only could have poor bactericidal activity and cause precipitation depending on the environment. A recent study revealed that gluconate of olanexidine has sufficient solubility in water, broad bactericidal spectrum, fast onset of the bactericidal effect and longer lasting bactericidal activity thereof, and thus that the gluconate serves as useful medical disinfectant (see patent document 1).

The above aqueous solution of olanexidine gluconate is colorless and transparent liquid. In contrast, povidone-iodine, used for preoperative skin disinfection, is a blackish brown liquid and thus the visual identification of the application sites could be easily performed. Chlorhexidine-alcohol, which is also used for preoperative skin disinfection, is naturally a colorless and transparent liquid, but the colored ones with dyes are also commercially available (e.g., "0.5% Hexizac Alcohol Solution", made by Yoshida Pharmaceutical Co., Ltd.).

PRIOR ART DOCUMENTS

Patent Documents

Patent Document 1
Japanese unexamined Patent Application Publication No. 2005-289959

Non-Patent Documents

Non-Patent Document 1
NAGAI Isao, et al., KankyoKansen, 15(3), 220 (2000)

SUMMARY OF THE INVENTION

Objects to be Solved by the Invention

The object of the present invention is to provide a disinfectant liquid enabling easy identification of the application sites in preoperative skin disinfection and the like, where the liquid is obtained by coloring an aqueous solution of olanexidine gluconate which is a colorless and transparent liquid.

Means to Solve the Object

The present inventors first tried adding several coloring agents to the aqueous solution of olanexidine gluconate, but the solution had precipitation thus found not to be suitable for practical use. To suppress the precipitation, we further added some surfactants to the solution and evaluated the bactericidal efficacy on 8 kinds of test bacteria: *Staphylococcus aureus* ATCC29213; *Enterococcus faecalis* ATCC15606; *Staphylococcus epidermidis* ATCC12228; *Serratia marcescens* ATCC14756; *Acinetobacter baumannii* ATCC19606; *Escherichia coli* ATCC25922; *Pseudomonas aeruginosa* ATCC27853; *Candida albicans* ATCC90028. The result showed that the bactericidal efficacy of olanexidine gluconate on the test bacteria, *Candida albicans* ATCC90028, was reduced. The present inventors have intensively studied for surfactants to be added and found that the addition of alkyl dimethylamine oxide could suppress the precipitation without reducing the bactericidal efficacy of olanexidine gluconate. Further, the present inventors have also found that the addition of alkyl dimethylamine oxide could prevent the reduction of bactericidal efficacy of olanexidine gluconate caused by other surfactants, and finally achieved the present invention.

Thus, the present invention is as follows:

(1) A composition for skin disinfection comprising olanexidine gluconate, a coloring agent, and alkyl dimethylamine oxide.
(2) The composition for skin disinfection according to the above (1), wherein the olanexidine gluconate has a concentration of 0.01 to 20 (W/V) %.
(3) The composition for skin disinfection according to the above (1) or (2), wherein the coloring agent is a legal tar dye.
(4) The composition for skin disinfection according to the above (3), wherein the legal tar dye is Sunset Yellow FCF.
(5) The composition for skin disinfection according to any one of the above (1) to (4), wherein the alkyl dimethylamine oxide has a concentration of 0.01 (W/V) % or more.
(6) The composition for skin disinfection according to any one of the above (1) to (5), further comprising polyoxyethylene alkyl ether.
(7) The composition for skin disinfection according to the above (6), wherein the ratio of the concentration of alkyl dimethylamine oxide to the total concentration of alkyl dimethylamine oxide and polyoxyethylene alkyl ether is 0.18 or more.
(8) The composition for skin disinfection according to any one of the above (1) to (5), further comprising polyoxyethylene polyoxypropylene alkyl ether.
(9) The composition for skin disinfection according to the above (8), wherein the ratio of the concentration of alkyl dimethylamine oxide to the total concentration of alkyl dimethylamine oxide and polyoxyethylene polyoxypropylene alkyl ether is 0.12 or more.
(10) The composition for skin disinfection according to any one of the above (1) to (5), further comprising polyoxyethylene alkyl ether and polyoxyethylene polyoxypropylene alkyl ether.
(11) The composition for skin disinfection according to the above (10), wherein the ratio of the concentration of alkyl dimethylamine oxide to the total concentration of alkyl dimethylamine oxide, polyoxyethylene alkyl ether and polyoxyethylene polyoxypropylene alkyl ether is 0.28 or more.
(12) The composition for skin disinfection according to any one of the above (1) to (11), wherein the alkyl dimethylamine oxide is alkyl dimethylamine oxide having an alkyl group with 10-16 carbon atoms.
(13) The composition for skin disinfection according to the above (12), wherein the alkyl dimethylamine oxide is selected from lauryl dimethylamine oxide, decyl dimethylamine oxide, myristyl dimethylamine oxide, and cocoalkyl dimethylamine oxide;

(14) The composition for skin disinfection according to any one of the above (6) to (7) and (10) to (13), wherein the polyoxyethylene alkyl ether is lauromacrogol.
(15) The composition for skin disinfection according to any one of the above (8) to (14), wherein the polyoxyethylene polyoxypropylene alkyl ether is polyoxyethylene(20) polyoxypropylene(4) cetyl ether.

Effect of the Invention

According to the composition of the present invention, the composition enables easy identification of the application sites of disinfectant liquid in preoperative skin disinfection and the like, and thus enables to complete disinfection with reliability and shortly.

BRIEF DESCRIPTION OF DRAWINGS

FIG. 1 is a table showing the bactericidal efficacy of the colored Olanedine disinfectant liquid formulation in Example 1 which comprises lauromacrogol as surfactant.

FIG. 2 is a table showing Log Reduction of the bactericidal efficacy of the colored Olanedine disinfectant liquid formulation in Example 1 which comprises lauromacrogol as surfactant.

FIG. 3 is a table showing the bactericidal efficacy of the colored Olanedine disinfectant liquid formulation in Example 2.

FIG. 4 is a table showing Log Reduction of the bactericidal efficacy of the colored Olanedine disinfectant liquid formulation in Example 2.

FIG. 5 is a table showing the bactericidal efficacy of the colored Olanedine disinfectant liquid formulations in Example 3.

FIG. 6 is a table showing Log Reduction of the bactericidal efficacy of the colored Olanedine disinfectant liquid formulation in Example 3.

FIG. 7 is a table showing the bactericidal efficacy of the colored Olanedine disinfectant liquid formulations in Example 4 which comprise, as surfactant, lauryl dimethylamine oxide alone (test numbers 1 to 3), lauryl dimethylamine oxide and lauromacrogol (test numbers 4 to 17), and lauromacrogol alone (test number 18).

FIG. 8 is a table showing Log Reduction of the bactericidal efficacy of the colored Olanedine disinfectant liquid formulation in Example 4 which comprise, as surfactant, lauryl dimethylamine oxide alone (test numbers 1 to 3), lauryl dimethylamine oxide and lauromacrogol (test numbers 4 to 17), and lauromacrogol alone (test number 18).

FIG. 9 is a table showing the bactericidal efficacy of the colored Olanedine disinfectant liquid formulation in Example 4 which comprise, as surfactant, lauryl dimethylamine oxide and polyoxyethylene(20) polyoxypropylene(4) cetyl ether.

FIG. 10 is a table showing Log Reduction of the bactericidal efficacy of the colored Olanedine disinfectant liquid formulation in Example 4 which comprise, as surfactant, lauryl dimethylamine oxide and polyoxyethylene(20) polyoxypropylene(4) cetyl ether.

FIG. 11 is a table showing the bactericidal efficacy of the colored Olanedine disinfectant liquid formulation in Example 3 which comprise, as surfactant, lauryl dimethylamine oxide, lauromacrogol and polyoxyethylene(20) polyoxypropylene(4) cetyl ether.

FIG. 12 is a table showing Log Reduction of the bactericidal efficacy of the colored Olanedine disinfectant liquid formulation in Example 4 which comprise, as surfactant, lauryl dimethylamine oxide, lauromacrogol and polyoxyethylene(20) polyoxypropylene(4) cetyl ether.

MODE OF CARRYING OUT THE INVENTION

The present invention relates to a composition for skin disinfection comprising olanexidine gluconate, a coloring agent, and alkyl dimethylamine oxide. The coloring agent can be any coloring agents as long as they are applicable to skin and can be natural coloring agents or synthetic coloring agents. Preferably tar dye (legal tar dye) that can be used in medicines, etc. based on the provisions of Article 56(7) of the Japanese Pharmaceutical Affairs Law (including when applied to Article 60 and Article 62) (Law No. 145 of 1960) is used. Examples of legal tar dye include amaranth (Red No. 2), New Coccine (Red No. 102), Orange II (Orange No. 205), Sunset Yellow FCF (Yellow No. 5), Tartrazine (Yellow No. 4), Erythrosine (Red No. 3), Phloxine B (Red No. 104), Rose Bengal (Red No. 105), Acid Red (Red No. 106), Fast Green FCF (Green No. 3), Brilliant Blue FCF (Blue No. 1), Indigo Carmine (Blue No. 2), Eosine YS (Red No. 230(1)), Uranine (Yellow No. 202(1)), Quinoline Yellow WS (Yellow No. 203), Alizarine Cyanine Green F (Green No. 201), Pyranine Conc (Green No. 204), Alphazurine FG (Blue No. 205), Lithol Rubine B (Red No. 201), Lithol Rubine BCA (Red No. 202), Lake Red C (Red No. 203), Lake Red CBA (Red No. 204), Lithol Red (Red No. 205), Lithol Red CA (Red No. 206), Lithol Red BA (Red No. 207), Lithol Red SR (Red No. 208), Rhodamine B (Red No. 213), Rhodamine B Acetate (Red No. 214), Rhodamine B Stearate (Red No. 215), Tetrachlorotetrabromofluorescein (Red No. 218), Brilliant Lake Red R (Red No. 219), Deep Maroon (Red No. 220), Toluidine Red (Red No. 221), Tetrabromofluorescein (Red No. 223), Sudan III (Red No. 225), Helindone Pink CN (Red No. 226), Fast Acid Magenta (Red No. 227), Permaton Red (Red No. 228), Phloxine BK (Red No. 231), Rose Bengal K (Red No. 232), Dibromofluorescein (Orange No. 201), Permanent Orange (Orange No. 203), Benzidine Orange G (Orange No. 204), Diiodofluorescein (Orange No. 206), Erythrosine Yellowish NA (Orange No. 207), Fluorescein (Yellow No. 201), Quinoline Yellow SS (Yellow No. 204), Benzidine Yellow G (Yellow No. 205), Quinizaline Green SS (Green No. 202), Light Green SF Yellowish (Green No. 205), Indigo (Blue No. 201), Patent Blue NA (Blue No. 202), Patent Blue CA (Blue No. 203), Carbanthrene Blue (Blue No. 204), Resorcin Brown (Brown No. 201), Alizurine Purple SS (Purple No. 201), Violamine R (Red No. 401), Brilliant Fast Scarlet (Red No. 404), Permanent Red F5R (Red No. 405), Scarlet Red NF (Red No. 501), Ponceau 3R (Red No. 502), Ponceau R (Red No. 503), Ponceau SX (Red No. 504), Oil Red XO (Red No. 505), Fast Red S (Red No. 506), Hanza Orange (Orange No. 401), Orange I (Orange No. 402), Orange SS (Orange No. 403), Hanza Yellow (Yellow No. 401), Polar Yellow 5G (Yellow No. 402), Naphthol Yellow S (Yellow No. 403(1)), Yellow AB (Yellow No. 404), Yellow OB (Yellow No. 405), Metanil Yellow (Yellow No. 406), Fast Light Yellow 3G (Yellow No. 407), Naphtol Green B (Green No. 401), Guinea Green B (Green No. 402), Sudan Blue B (Blue No. 403), Phtalocyanine Blue (Blue No. 404), Alizurol Purple (Purple No. 401), Naphthol Blue Black (Black No. 401), Eosine YSK (Red No. 230(2)) and Uranine K (Yellow No. 202). Furthermore Sunset Yellow FCF (Yellow No. 5) is preferably used.

The concentration of olanexidine gluconate is not particularly limited as long as that provides sufficient bactericidal efficacy. The concentration can be, for example, 0.01 to 20 (W/V) %, further preferably 0.1 to 10 (W/V) %, furthermore preferably 1 to 5 (W/V) %.

In the present invention, the alkyl dimethylamine oxide is added to suppress the precipitation caused by the addition of coloring agent and/or to prevent the reduction of the bactericidal efficacy of olanexidine gluconate caused by the addition of surfactants other than alkyl dimethylamine oxide. The alkyl dimethylamine oxide which can be used in the present invention can include oleyl dimethylamine oxide, stearyl dimethylamine oxide, isostearyl dimethylamine oxide, palmityl dimethylamine oxide, myristyl dimethylamine oxide, lauryl dimethylamine oxide, capryl dimethylamine oxide, cocoalkyl dimethylamine oxide, octyl dimethylamine oxide, nonyl dimethylamine oxide, decyl dimethylamine oxide, undecyl dimethylamine oxide, dodecyl dimethylamine oxide, isododecyl dimethylamine oxide, tridecyl dimethylamine oxide, tetradecyl dimethylamine oxide, pentadecyl dimethylamine oxide, hexadecyldimethylamine oxide, heptadecyl dimethylamine oxide, octadecyl dimethylamine oxide. Preferably, alkyl dimethylamine oxide having an alkyl group with 10-16 carbon atoms, and especially, lauryl dimethylamine oxide, decyl dimethylamine oxide, myristyl dimethylamine oxide, and cocoalkyl dimethylamine oxide can be suitably included.

The concentration of alkyl dimethylamine oxide can be, for example, 0.01 (W/V) % or more, 0.02 (W/V) % or more, 0.05 (W/V) % or more, preferably 0.1 (W/V) % or more, 0.2 (W/V) % or more, 0.5 (W/V) % or more, further preferably 1.0 (W/V) % or more, 1.5 (W/V) % or more, furthermore preferably 2.0 (W/V) % or more, 2.5 (W/V) % or more, 3.0 (W/V) % or more, and the upper limit can be, without particular limitations, for example, 25 (W/V) % or less, preferably 20 (W/V) % or less, further preferably 15 (W/V) % or less.

The composition of the present invention can further include one or more surfactants other than alkyl dimethylamine oxide. The surfactants other than alkyl dimethylamine oxide can include, for example, sorbitan fatty acid ester, polyoxyethylene sorbitan fatty acid ester, polyoxyethylene alkyl ether, polyoxyethylene polyoxypropylene alkyl ether, polyoxyethylene polyoxypropylene glycol, polyglyceryl fatty acid ester, polyoxyethylene hardened castor oil and sucrose fatty acid ester, and especially polyoxyethylene alkyl ether and polyoxyethylene polyoxypropylene alkyl ether are preferable. The polyoxyethylene alkyl ether can include polyoxyethylene cetyl ether, polyoxyethylene oleyl ether and polyoxyethylene lauryl ether, and especially polyoxyethylene lauryl ether (lauromacrogol) is preferable. The polyoxyethylene polyoxypropylene alkyl ether can include polyoxyethylene(20) polyoxypropylene(4) cetyl ether, polyoxyethylene(30) polyoxypropylene(6) decyl tetradecyl ether and polyoxyethylene(25) polyoxypropylene(25) lauryl ether, and especially polyoxyethylene(20) polyoxypropylene(4) cetyl ether is preferable.

When the composition of the present invention further comprises one or more surfactants other than alkyl dimethylamine oxide, the ratio of the concentration of alkyl dimethylamine oxide to the total concentration of surfactant is desirably not less than a predetermined ratio in order to prevent the reduction of bactericidal efficacy of olanexidine gluconate. The predetermined ratio can be, for example, preferably 0.08 or more, further preferably 0.12 or more, furthermore preferably 0.28 or more, and especially preferably 0.5 or more.

When the composition of the present invention comprises polyoxyethylene alkyl ether, the ratio of the concentration of alkyl dimethylamine oxide to the total concentration of alkyl dimethylamine oxide and polyoxyethylene alkyl ether can be, for example, preferably 0.12 or more, further preferably 0.18 or more, and furthermore preferably 0.5 or more.

When the composition of the present invention comprises polyoxyethylene polyoxypropylene alkyl ether, the ratio of the concentration of alkyl dimethylamine oxide to the total concentration of alkyl dimethylamine oxide and polyoxyethylene polyoxypropylene alkyl ether can be, for example, preferably 0.12 or more, further preferably 0.18 or more, and furthermore preferably 0.5 or more.

When the composition of the present invention comprises polyoxyethylene alkyl ether and polyoxyethylene polyoxypropylene alkyl ether, the ratio of the concentration of alkyl dimethylamine oxide to the total concentration of alkyl dimethylamine oxide, polyoxyethylene alkyl ether and polyoxyethylene polyoxypropylene alkyl ether can be, for example, preferably 0.08 or more, further preferably 0.28 or more, and furthermore preferably 0.5 or more.

The composition of the present invention can be applied to any surface to be disinfected, by any known methods and means. For example, the composition can be applied to the surface by cloth, absorbent cotton, a swab, sponge, facial tissue, a paper towel or the like, or can be splayed to the surface, or can be applied to the surface by any known applicators.

Hereinafter, the present invention will be described in more details by the following Examples. However, the technical scope of the present invention is not limited thereto.

Example 1

1. Evaluation of Bactericidal Efficacy of the Colored Olanedine Disinfectant Liquid Formulation The present inventors confirmed in a preliminary test that addition of Sunset Yellow FCF (Yellow No. 5) to 1.5% Olanedine solution (a solution containing 1.508 (W/V) % olanexidine gluconate, made by Otsuka Pharmaceutical Factory, Inc.) caused the precipitation. To dissolve the precipitation caused by the addition of Sunset Yellow FCF (Yellow No. 5), a colored formulation (colored Olanedine disinfectant liquid formulation) containing lauromacrogol as surfactant to be the final concentration of 2 (W/V) % was prepared, and the formulation was tested for the bactericidal efficacy.

1-1 Reagents and Culture Medium

The amounts produced were varied depending on the amount used, where the amounts of reagents, culture medium and solvent were increased and decreased at the constant ratio.

1-1-1 Neutralizer 10.0 g of polysorbate 80 was weighted out, to which about 80 mL of distilled water and 1.17 g of soy lecithin were added, and the mixture was heated and stirred. To the mixture, 1.01 g of disodium hydrogen phosphate, 0.04 g of potassium dihydrogen phosphate, 0.5 g of sodium thiosulfate hydrate, and 1.0 g of Tamol (Registered trademark) NN 8906 were added, and the obtained mixture was heated and stirred until they dissolved. After dissolution, the solution was cooled to room temperature, and adjusted to pH 7.8 to 7.9 with an aqueous sodium hydroxide solution or hydrochloric acid. Distilled water was added to the solution to be the total amount of 100 mL and the obtained solution was subjected to high pressure steam sterilization (121° C., 20 minutes).

1-1-2 SABLP Culture Medium 73.0 g of Sabouraud-Dextrose Agar with Lecithin & Polysorbate (SABLP) culture medium, composed of 40.0 g/L of dextrose, 10.0 g/L of peptone, 15.0 g/L of agar, 1.0 g/L of lecithin, and 7.0 g/L of polysorbate 80, was weighted out into glass Erlenmeyer flask. 1000 mL of pure water was added to the medium, and the mixture was stirred with stirrer. The obtained medium was subjected to high pressure steam sterilization (121° C., 20 minutes), then stored in a hot bath set at 47° C. until use.

1-1-3 Test Substance

A trace amount of Sunset. Yellow FCF (Yellow No. 5) and lauromacrogol at the final concentration of 2 (W/V) % was added to 1.5 (W/V) % olanexidine gluconate to prepare the test substance.

1-2 Test Procedure 1-2-1 Preparation of Test Bacterial Solution

Colonies of 8 kinds of the test bacteria: *Staphylococcus aureus* ATCC29213; *Enterococcus faecalis* ATCC15606; *Staphylococcus epidermidis* ATCC12228; *Serratia marcescens* ATCC14756; *Acinetobacter baumannii* ATCC19606; *Escherichia coli* ATCC25922; *Pseudomonas aeruginosa* ATCC27853; *Candida albicans* ATCC90028 grown on the SABLP culture medium were collected with platinum loop and to the colonies was added distilled water to prepare McFarland 5 bacterial solution. The obtained solution was used as a test bacterial solution.

1-2-2 Measurement of Initial Viable Cell Count

150 μL of the test bacterial solution was added to 3 mL of distilled water, and mixed well. Immediately, 0.5 mL of the mixed bacterial solution was added to 4.5 mL of neutralizer, and mixed well. The obtained solution was used as a $10^1$-fold diluted solution. Then, 0.5 mL of the $10^1$-fold diluted solution was added to 4.5 mL of a neutralizer to dilute the solution a further 10-fold. Dilution was repeated according to the same procedure to make serial 10-fold dilutions (composed of total 5 levels ranging from $10^1$ to $10^5$-fold diluted solutions). Each of the $10^3$ to $10^5$-fold diluted solution was dispensed in 1 mL-portions to petri dishes, and about 15 mL of the SABLP culture medium stored in a hot bath were added to each of the dishes to prepare pour plates. After solidification, the pour plates were inverted and aerobically cultured at 35±2° C. for 2 days. The number of colonies grown on the pour plates was visually counted. This procedure was repeated three times.

1-2-3 Measurement of Viable Cell Count after Action of Test Substance

To 3 mL of each test substance was added 150 μL of the test bacterial solution, and mixed well. The obtained solution was used as reaction solution. The reaction was carried out at room temperature (23.0±3.0° C.). After 30 and 60 seconds from the reaction, 0.5 mL of the reaction solution was added to 4.5 mL of neutralizer and mixed well. The obtained solution was used as a $10^1$-fold diluted solution. Then, 0.5 mL of the $10^1$-fold diluted solution was added to 4.5 mL of neutralizer to dilute the solution a further 10-fold. The obtained solution was used as a $10^2$-fold diluted solution. Each of $10^1$ and $10^2$-fold diluted solutions was dispensed in 1 mL-portions to petri dishes, and to which about 15 mL of the SABLP culture medium stored in a hot bath were added to prepare pour plates. After solidification, the pour plates were inverted and aerobically cultured at 35±2° C. for 2 days. The number of colonies grown on the pour plates was visually counted. This procedure was repeated three times.

1-2-4 Calculation of Log Reduction

Initial viable cell count (CFU/mL) on common logarithmic value and the average value thereof were determined. This average value and the average value of viable cell count after action of the test substance for each period (CFU/mL) on logarithmic value were used to calculate Log Reduction by the following formula:

$$\text{Log Reduction} = B - C$$

B: The average value of initial viable cell count (common logarithmic value)
C: The average value of viable cell count after action of each test substance (common logarithmic value)

1-3 Results

The results are shown in FIGS. 1 and 2. In FIG. 1, circles (○) indicate the composition having bactericidal efficacy (the composition having the same number of colonies grown on the pour plate as that of the colorless Olanedine disinfectant liquid formulation in "1-2-3 Measurement of viable cell count after action of test substance"). FIG. 2 shows Log Reduction of the bactericidal efficacy of the colored Olanedine disinfectant liquid formulation. Regarding the test bacteria other than *Candida albicans* ATCC90028, the colored Olanedine disinfectant liquid formulation had the bactericidal efficacy similar to that of the conventional colorless Olanedine disinfectant liquid formulation, while regarding *Candida albicans* ATCC90028, the bactericidal efficacy of the colored Olanedine disinfectant liquid formulation was reduced in 30 seconds.

Example 2

2. Study 1 for Surfactant

Example 1 demonstrated that the use of lauromacrogol as surfactant reduced the bactericidal efficacy on *Candida albicans* ATCC90028 of the colored Olanedine disinfectant liquid formulation. In this test, various surfactants were used to prepare the colored Olanedine disinfectant liquid formulations, and their bactericidal efficacy on *Candida albicans* ATCC90028 was tested.

2-1 Test Procedure

The test procedure was the same as in Example 1, except that the test substance was an aqueous solution of 1.5 (W/V) % olanexidine gluconate containing a trace amount of Sunset Yellow FCF (Yellow No. 5) and surfactants described in FIGS. 3 and 4, and that the test bacteria was *Candida albicans* ATCC90028.

2-2 Results

The results are shown in FIGS. 3 and 4.

In FIG. 3, circles (○) indicate the composition having bactericidal efficacy (the composition having the same number of colonies grown on the pour plate as that of the colorless Olanedine disinfectant liquid formulation in "1-2-3 Measurement of viable cell count after action of test substance"). The composition using 2.4 (W/V) % lauryl dimethylamine oxide as surfactant didn't show the reduction of bactericidal efficacy in 30 and 60 seconds, while the composition using 2 (W/V) % lauromacrogol showed the reduction of bactericidal efficacy in 60 seconds only, and the compositions using 3.6 (W/V) % polyoxyethylene(20) polyoxypropylene(8) glycol and 6 (W/V) % polyoxyethylene hardened castor oil 60 showed the reduction of bactericidal efficacy in both of 30 and 60 seconds.

FIG. 4 shows Log Reduction of the currently used colorless Olanedine disinfectant liquid formulation, and Log Reduction of the colored Olanedine disinfectant liquid formulations using 2 (W/V) % lauromacrogol, 3.6 (W/V) % polyoxyethylene(20) polyoxypropylene(8) glycol, 6 (W/V) % polyoxyethylene hardened castor oil 60, or 2.4 (W/V) % lauryl dimethylamine oxide as surfactant. The colored Olanedine disinfectant liquid formulation using 2.4 (W/V)

% lauryl dimethylamine oxide showed Log Reduction equivalent to that of the currently used colorless Olanedine disinfectant liquid formulation. While the colored Olanedine disinfectant liquid formulations using the other surfactants showed lower Log Reduction than that of the currently used colorless Olanedine disinfectant liquid formulation.

Example 3

3. Study 2 for Surfactant

Example 2 demonstrated that when lauryl dimethylamine oxide which is alkyl dimethylamine oxide is used as surfactant, the colored Olanedine disinfectant liquid formulation, which have bactericidal efficacy similar to that of the currently used colorless Olanedine disinfectant liquid formulation, can be prepared. In this test, alkyl dimethylamine oxide other than lauryl dimethylamine oxide was used to prepare the colored Olanedine disinfectant liquid formulations, and the formulations were tested for the bactericidal efficacy.

3-1 Test Procedure

The test procedure was the same as in Example 1, except that the test substances were aqueous solutions of 1.5 (W/V) % olanexidine gluconate containing a trace amount of Sunset Yellow FCF (Yellow No. 5) and surfactants described in Figures and 6 and that the test bacteria was *Candida albicans* ATCC90028.

3-2 Results

The results are shown in FIGS. 5 and 6.

In FIG. 5, circles (○) indicate the composition having bactericidal efficacy (the composition having the same number of colonies grown on the pour plate as that of the colorless Olanedine disinfectant liquid formulation in "1-2-3 Measurement of viable cell count after action of test substance"). The composition using 2.5 (W/V) % decyl dimethylamine oxide, 2.5 (W/V) % myristyl dimethylamine oxide or 2.5 (W/V) % cocoalkyl dimethylamine oxide, didn't show the reduction of bactericidal efficacy in 30 and 60 seconds, similarly as when using 2.5 (W/V) % lauryl dimethylamine oxide.

FIG. 6 shows Log Reduction of the currently used colorless Olanedine disinfectant liquid formulation, and Log Reduction of the colored Olanedine disinfectant liquid formulations using 2.5 (W/V) % lauryl dimethylamine oxide, 2.5 (W/V) % decyl dimethylamine oxide, 2.5 (W/V) % myristyl dimethylamine oxide or 2.5 (W/V) % cocoalkyl dimethylamine oxide as surfactant. The Olanedine disinfectant liquid formulation using any of the surfactants tested in the Example showed Log Reduction equivalent to that of the currently used colorless Olanedine disinfectant liquid formulation.

Example 4

4. Study 3 for Surfactant

Example 2 demonstrated that when lauryl dimethylamine oxide as surfactant is used, the colored Olanedine disinfectant liquid formulation, which have bactericidal efficacy similar to that of the currently used colorless Olanedine disinfectant liquid formulation, can be prepared. In this test, lauryl dimethylamine oxide combined with other surfactants was used to prepare the colored Olanedine disinfectant liquid formulations, and the formulations were tested for the bactericidal efficacy.

4-1 Test Procedure

The test procedure was the same as in Example 1, except that the test substances were aqueous solutions of 1.5 (W/V) % olanexidine gluconate containing a trace amount of Sunset Yellow FCF (Yellow No. 5) and surfactants described in FIGS. 7 to 12 and that the test bacteria was *Candida albicans* ATCC90028. In the Figures, LDAO represents lauryl dimethylamine oxide, a cationic surfactant, and POE (20) POP(4) cetyl ether represents polyoxyethylene(20) polyoxypropylene(4) cetyl ether.

4-2 Results

The results are shown in FIGS. 7 to 12. In FIGS. 7, 9 and 11, circles (○) indicate the composition having bactericidal efficacy (the composition having the same number of colonies grown on the pour plate as that of the colorless Olanedine disinfectant liquid formulation in "1-2-3 Measurement of viable cell count after action of test substance").

4-2-1 the Bactericidal Efficacy of the Composition with the Addition of LDAO

The results are shown in FIGS. 5 and 6 at the test numbers 1 to 3. The composition didn't show the reduction of bactericidal efficacy in 30 and 60 seconds despite the addition amount of LDAO. Test number 1 demonstrated that the precipitation caused by the addition of coloring agent to 1.5 (W/V) % olanexidine gluconate was dissolved by using 2.0 (W/V) % lauryl dimethylamine oxide. This result suggested that the precipitation caused by the addition of coloring agent to 0.01 (W/V) % olanexidine gluconate can be dissolved by using 0.013 (W/V) % lauryl dimethylamine oxide.

4-2-2 the Bactericidal Efficacy of the Composition with the Addition of LDAO and Lauromacrogol The results are shown in FIGS. 7 and 8 at the test numbers 4 to 18. The composition containing lauromacrogol alone showed the reduction of bactericidal efficacy in 30 seconds (FIG. 7, test number 18). While, the composition containing lauromacrogol and LDAO, at the ratio of the concentration of LDAO to the total concentration of lauromacrogol and LDAO being 0.18 or more, didn't show the reduction of bactericidal efficacy in 30 and 60 seconds.

4-2-3 the Bactericidal Efficacy of the Composition with the Addition of LDAO and POE(20) POP(4) Cetyl Ether.

The results are shown in FIGS. 9 and 10. The composition containing POE(20) POP(4) cetyl ether alone showed the reduction of bactericidal efficacy in 30 and 60 seconds. While, the composition containing POE(20) POP(4) cetyl ether and LDAO, at the ratio of the concentration of LDAO to the total concentration of POE(20) POP(4) cetyl ether and LDAO being 0.12 or more, didn't show the reduction of bactericidal efficacy in 30 and 60 seconds.

4-2-4 the Bactericidal Efficacy of the Composition with the Addition of LDAO, Lauromacrogol and POE(20) POP (4) Cetyl Ether The results are shown in FIGS. 11 and 12. The composition at the ratio of the concentration of LDAO to the total concentration of LDAO, lauromacrogol and POE(20) POP (4) cetyl ether being 0.06 or more, didn't show the reduction of bactericidal efficacy in 60 seconds, and the composition at the ratio being 0.28 or more didn't show the reduction of bactericidal efficacy in 30 and 60 seconds.

INDUSTRIAL APPLICABILITY

The composition of the present invention enables easy application of olanexidine gluconate in skin disinfection and the like, where the olanexidine gluconate has broad bactericidal spectrum, fast onset of the bactericidal effect and longer lasting bactericidal activity thereof. Thus the composition of the present invention has high industrial applicability in the medical field.

The invention claimed is:

1. A composition for skin disinfection comprising olanexidine gluconate, a coloring agent, alkyl dimethylamine oxide, and 0 (W/V) % to 4 (W/V) % of polyoxyethylene alkyl ether, wherein the ratio of the concentration of alkyl dimethylamine oxide to the total concentration of alkyl dimethylamine oxide and polyoxyethylene alkyl ether is 0.18 or more.

2. The composition for skin disinfection according to claim 1, wherein the olanexidine gluconate has a concentration of 0.01 to 20 (W/V) %.

3. The composition for skin disinfection according to claim 1, wherein the coloring agent is a legal tar dye.

4. The composition for skin disinfection according to claim 3, wherein the legal tar dye is Sunset Yellow FCF.

5. The composition for skin disinfection according to claim 1, wherein the alkyl dimethylamine oxide has a concentration of 0.01 (W/V) % or more.

6. The composition for skin disinfection according to claim 1, comprising polyoxyethylene alkyl ether.

7. The composition for skin disinfection according to claim 1, further comprising polyoxyethylene polyoxypropylene alkyl ether.

8. The composition for skin disinfection according to claim 7, wherein the ratio of the concentration of alkyl dimethylamine oxide to the total concentration of alkyl dimethylamine oxide and polyoxyethylene polyoxypropylene alkyl ether is 0.12 or more.

9. The composition for skin disinfection according to claim 6, further comprising polyoxyethylene polyoxypropylene alkyl ether.

10. The composition for skin disinfection according to claim 9, wherein the ratio of the concentration of alkyl dimethylamine oxide to the total concentration of alkyl dimethylamine oxide, polyoxyethylene alkyl ether and polyoxyethylene polyoxypropylene alkyl ether is 0.28 or more.

11. The composition for skin disinfection according to claim 1, wherein the alkyl dimethylamine oxide is alkyl dimethylamine oxide having an alkyl group with 10-16 carbon atoms.

12. The composition for skin disinfection according to claim 11, wherein the alkyl dimethylamine oxide is selected from lauryl dimethylamine oxide, decyl dimethylamine oxide, myristyl dimethylamine oxide, and cocoalkyl dimethylamine oxide.

13. The composition for skin disinfection according to claim 1, wherein the polyoxyethylene alkyl ether is lauromacrogol.

14. The composition for skin disinfection according to claim 7, wherein the polyoxyethylene polyoxypropylene alkyl ether is polyoxyethylene(20) polyoxypropylene(4) cetyl ether.

15. The composition for skin disinfection according to claim 2, wherein the coloring agent is a legal tar dye.

16. The composition for skin disinfection according to claim 2, wherein the alkyl dimethylamine oxide has a concentration of 0.01 (W/V) % or more.

17. The composition for skin disinfection according to claim 3, wherein the alkyl dimethylamine oxide has a concentration of 0.01 (W/V) % or more.

18. The composition for skin disinfection according to claim 4, wherein the alkyl dimethylamine oxide has a concentration of 0.01 (W/V) % or more.

19. The composition for skin disinfection according to claim 15, wherein the alkyl dimethylamine oxide has a concentration of 0.01 (W/V) % or more.

* * * * *